United States Patent [19]

Ogiu et al.

[11] 4,235,238

[45] Nov. 25, 1980

[54] APPARATUS FOR SUTURING COELIAC TISSUES

[75] Inventors: Hisao Ogiu; Hideki Shimonaka, both of Hachioji, Japan

[73] Assignee: Olympus Optical Co., Ltd., Tokyo, Japan

[21] Appl. No.: 35,805

[22] Filed: May 4, 1979

[30] Foreign Application Priority Data

| May 11, 1978 | [JP] | Japan | 53-62911 |
| May 11, 1978 | [JP] | Japan | 53-62912 |
| Jun. 1, 1978 | [JP] | Japan | 53-74942 |
| Jun. 8, 1978 | [JP] | Japan | 53-78230 |

[51] Int. Cl.³ .................................................. A61B 17/04
[52] U.S. Cl. .................................. 128/334 R; 128/335
[58] Field of Search ................... 128/334 R, 340, 335, 128/339, 330, 4, 329

[56] References Cited

U.S. PATENT DOCUMENTS

| 487,304 | 12/1892 | Todd | 128/330 |
| 1,059,631 | 4/1913 | Popovics | 128/330 |
| 3,470,875 | 10/1969 | Johnson | 128/334 R |
| 3,527,223 | 9/1970 | Shein | 128/329 |
| 3,643,649 | 2/1972 | Amato | 128/330 X |
| 4,006,747 | 2/1977 | Kronenthal et al. | 128/335 |
| 4,103,690 | 8/1978 | Harris | 128/334 R X |
| 4,160,453 | 7/1979 | Miller | 128/330 |

FOREIGN PATENT DOCUMENTS 401677  11/1933  United Kingdom ................ 128/334 R Primary Examiner—Lawrence W. Trapp

[57] ABSTRACT

A coeliac tissue-suturing apparatus comprising a flexible tubular member having a passage extending therethrough and inserted into a channel of an endoscope, a needle having one end concentrically fixed to that end of the tubular member which is inserted into the endoscope and having the other end made into a sharp tip, said needle having substantially the same outer diameter as the tubular member and adapted to protrude from a distal end of the endoscope, a first-stop receiving chamber communicating with the atmosphere and the passage of the tubular member, a first stop for setting suturing thread on tissues around a coeliac bleeding spot at the commencement of a suturing operation, said first stop being adapted to fix one end of the suturing thread extended along the tubular member, and normally received in the first-stop receiving chamber, and a pushing member inserted into the tubular member for pushing the first stop out of the first stop-receiving chamber.

28 Claims, 56 Drawing Figures

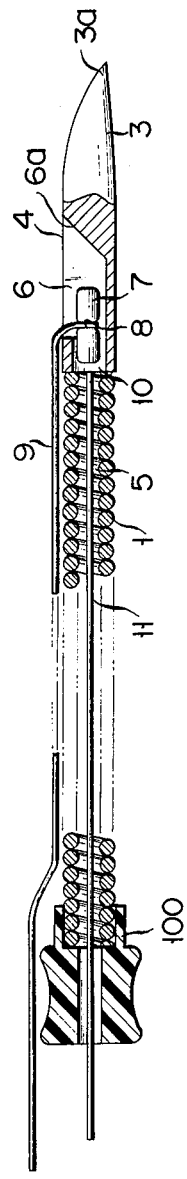
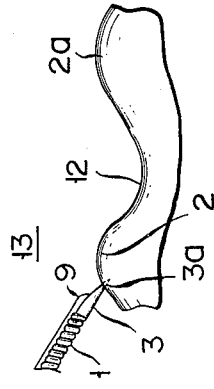
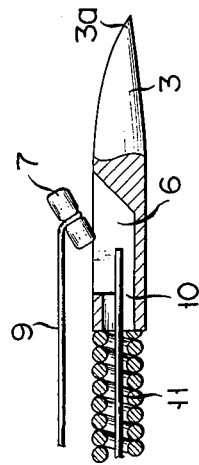
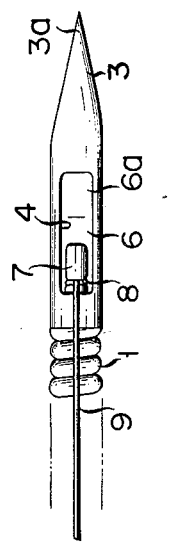
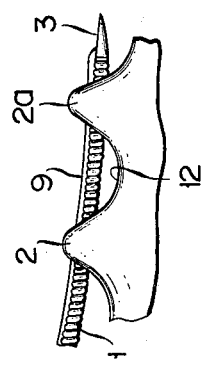

F I G. 11
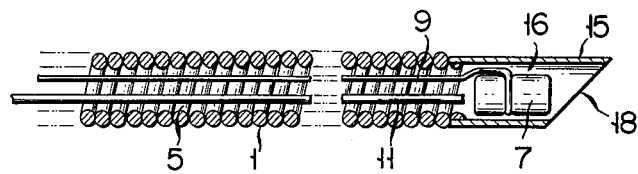
F I G. 12
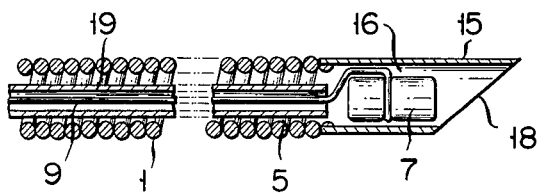
F I G. 13
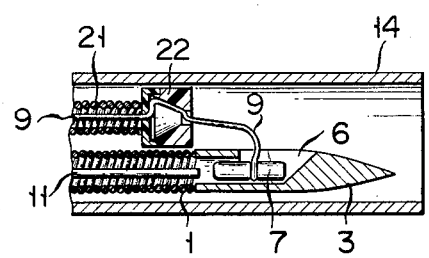
F I G. 14
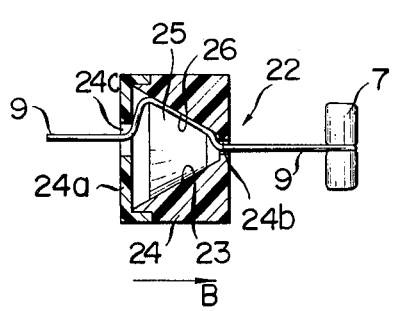
F I G. 15
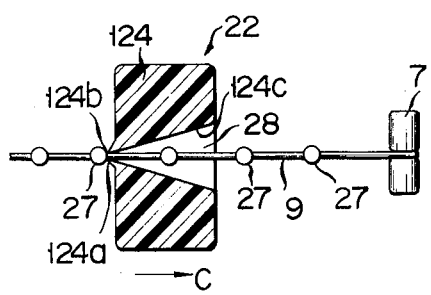

APPARATUS FOR SUTURING COELIAC TISSUES

BACKGROUND OF THE INVENTION

This invention relates to a suturing apparatus conducted into a body cavity through an endoscope to suture tissues around a bleeding portion in the body cavity.

The known endoscope type hemostatic method for a coeliac bleeding spot includes the step (as set forth in the published Japanese utility model No. 20957/1978) of conducting a clip through the endoscope to the bleeding spot to clamp tissues around the bleeding spot, and the step of protruding a metal tip from the distal end of the endoscope, contacting it with the bleeding spot and introducing high frequency current therethrough to cauterize the bleeding spot.

However, the process of using the clip has the drawbacks that since the clip can generally be opened to an extent of 10 millimeters at most, it is impossible to clamp tissues around a bleeding spot by the clip, if the bleeding spot is nearly as large as or larger than the extent to which the clip can be opened; the bleeding spot cannot sometimes be unfailingly clamped due to the weak gripping strength of the clip; if tissues held by the clip are too soft, they tend to be torn off, rather resulting in the widening of the bleeding spot; and consequently the clip sometimes comes off from the tissues, failing to carry out a hemostatic action.

Further, it is impossible to uniformly cauterize a broad bleeding spot by high frequency current.

As mentioned above, the prior art hemostatic method has proved unadapted for a considerably larger coeliac bleeding spot, though effective if said bleeding spot is relatively small.

SUMMARY OF THE INVENTION

It is accordingly the object of this invention to provide a coeliac tissue-suturing apparatus in which a needle is conducted through an endoscope into a body cavity to suture a broad coeliac bleeding spot, thereby unfailing carrying out a hemostatic operation.

To attain the above-mentioned object this invention provides a coeliac tissue-suturing apparatus which comprises a flexible tubular member to be conducted through a channel of an endoscope; a needle protrudable from the distal end of the endoscope, one end of the needle being concentrically fixed to that end of the tubular member at which it is inserted into the endoscope, and the other end of the needle being formed into a sharp tip; a stop receiving chamber provided in the needle and made to communicate with the outside area of the needle and the interior of the tubular member; a stop which is normally held in said stop receiving chamber, and to which a suturing thread extended along the tubular member is fixed at one end; and a pushing member for forcing the stop out of the chamber when inserted into the tubular member.

The above-mentioned suturing apparatus embodying this invention enables a coeliac bleeding spot to be reliably sutured by a needle and thread, thereby easily effecting a hemostatic operation, no matter how widely the bleeding spot is extended.

A bendable joint is provided between the needle and tubular member of the suturing apparatus, thereby ensuring the suture of slightly projecting tissues around a coeliac bleeding spot. Further, application of a plurality of stops, makes it possible to suture tissues around a broad coeliac bleeding spot with a single thread by carring out the suturing operation in the zig-zag form.

BRIEF DESCRIPTION OF THE DRAWING

This invention can be fully understood from the following description with reference to the accompanying drawings in which:

FIG. 1 is a longitudinal sectional view of a coeliac tissue-suturing apparatus according to one embodiment of this invention;

FIG. 2 is a flan view of the distal end portion of the suturing apparatus of FIG. 1;

FIG. 3 illustrates the condition in which a needle begins to be inserted into tisues around a coeliac bleeding spot;

FIG. 4 indicates the condition in which the suturing apparatus of FIG. 1 has penetrated tissues on both sides of the coeliac bleeding spot;

FIG. 5 shows the condition in which a stop has been forced by a pushing rod out of the stop-receiving chamber of the needle;

FIGS. 9 to 12 are, respectively, longitudinal sectional views of coeliac tissue-suturing apparatuses according to other embodiments of this invention;

FIG. 13 is a longitudinal sectional view of the main section of a coelic tissue-suturing apparatus according to another embodiment of the invention which contains an intermediate stop;

FIGS. 14 to 17 are, respectively, longitudinal sectional views of the modifications of the stop of FIG. 13;

DESCRIPTION OF THE PREFERRED EMBODIMENTS

Figure 6:
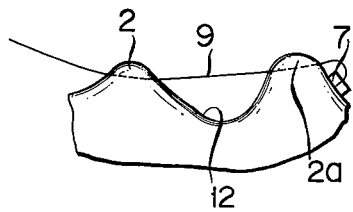
FIG. 6 indicates the condition in which a suturing thread remains in a state penetrating tissues around a bleeding spot, after the suturing apparatus of FIG. 1 has been pulled out.

Throughout the drawings, the same or similar parts are denoted by the same reference numerals.

Referring to FIGS. 1 and 2, a coeliac tissue-suturing apparatus embodying this invention comprises a flexible tubular member 1 constructed by winding a flexible wire such as stainless steel in the coil form. The distal end of the tubular member 1 is securely fitted with the rear end of a substantially cylindrical stainless steel needle 3 provided with a sharp tip 3a. The needle 3 is coaxial with the tubular member 1 and has the same outer diameter as the tubular member 1 so as to be easily inserted into the channel of an endoscope.

Formed in the body of the needle 3 is a first-stop receiving chamber 6 which is opened to the outside at the lateral opening 4 of the needle 3 and conunicates with the interior of the tubular member 1 or a cylindrical passage 5 through a cylindrical passage 10 formed in the rear end of the needle 3. The forward end portion of the first-stop receiving chamber 6 is constituted by an inclined wall 6a which progressively approaches the lateral wall of the needle 3 as it is drawn to the tip 3a of the needle 3. That end of a suturing thread 9 extended along the peripheral surface of the tubular member 1 which faces the needle 3 is fastened to a first pillar like or cylindrical stop 7 in a state inserted into an annular groove 8 formed at the center of the first stop 7. The first stop 7 is received in the receiving chamber 6, such that the rear end of the stop 7 is inserted into the passage 10, thereby preventing the stop 7 from naturally coming off.

Inserted into the tubular member 1 is a flexible pushing rod 11 made of, for example, a stainless steel wire. The rod 11 can be flexed in accordance with the bending of an endoscope channel, but has a sufficient rigidity to push the first stop 7 forward. The distal end of the pushing rod 11 inserted into the tubular member 1 pushes the first stop 7, which in turn slides up the inclined wall 6a of the first-stop receiving chamber 6 to protrude out of the needle 3 through its lateral opening 4 as shown in FIG. 5.

The tubular member 1 has an outer diameter of 1 to 1.5 millimeters. When the tubular member 1 is inserted into the channel of an endoscope and the needle 3 is brought to a bleeding spot 12 in a body cavity 13 (FIG. 3), the rear end of the tubular member 1 still protrudes from a proximal end of the endoscope. The protruding rear end of the tubular member 1 is fitted with a handle 100, which is operated by hand to reciprocate the tubular member 1 through the endoscope channel. The pushing rod 11 projects outward from the handle 100. The reciprocation of the tubular member 1 is effected by manipulating the protruding end of the pushing rod 11. The suturing thread 9 protrudes from the proximal end of the endoscope as much as needed.

There will now be described the operation of the apparatus of this invention for suturing tissues around a coeliac bleeding spot.

First, the suturing apparatus is inserted into a channel of an emdoscope from its proximal end with the needle 3 set in a forward position. While the interior of the body cavity 13 is observed by the endoscope, the suturing apparatus is moved back and forth by manually operating the handle 100 in order to let the tip 3a of the needle 3 be drawn near, as shown in FIG. 3, to those tissues around the bleeding spot 12 which lie close to the distal end of the endoscope. The needle 3 is let prick the tissue at a proper angle. Thereafter, the distal end of the endoscope is lifted to push tissues upward in FIG. 3. The tubular member 1 is further inserted forward through the endoscope channel to penetrate the tissues 2. Then, the distal end of the endoscope is brought down to cause the tip 3a of the needle 3 to approach tissues 2a lying beyond the bleeding spot 12. Later, the suturing apparatus is operated in the same manner as when the tissues 2 are treated, causing the needle 3 to penetrate the tissues 2, 2a lying on both sides of the bleeding spot 12 (FIG. 4).

Figure 7:
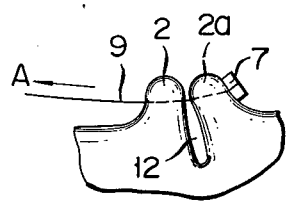
FIG. 7 illustrates the condition in which tissues around a bleeding spot are sewn together by retracting a suturing thread, thereby closing the bleeding spot.
Figure 8:
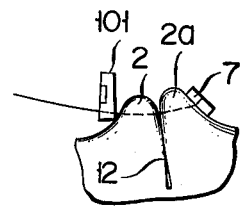
FIG. 8 shows the condition in which a clip holds that portion of a suturing thread penetrating the sutured tissues which faces the opposite side of the tissues to the stop.

The pushing rod 11 is inserted into the tubular member 1 by operating the handle 100 to cause the first stop 7 to slide up the inclined wall 6a out of the stop receiving chamber 6 by the action of the distal end of the pushing rod 11 and enter the body cavity through the lateral opening 4 of the needle 3 (FIG. 5). When the suturing apparatus is pulled out of the fissues 2, 2a, the suturing thread 9 passes through the tissues 2, 2a with the stop 7 left on the opposite side of the tissues 2a to the bleeding spot 12. When the suturing thread 9 is pulled in the direction of an arrow A indicated in FIG. 7, the tissures 2, 2a are drawn to each other. As a result, the bleeding spot 12 is shaped like a deep groove, and the tissues 2, 2a are tightly attached to each other as shown in FIG. 8. At this time, that portion of the suturing thread 9 which faces the opposite side of the tissue 2 to the bleeding spot 12 is clampled by a clip 101 conducted through another endoscope channel by the known process. That portion of the suturing thread 9 which faces the opposite side of the clip 101 to the tissue 2 is cut by a cutting device set forth in, for example, the Japanese utility model publication No. 23672/1974. Thus, a broad bleeding spot 12 as occurring in the case of an ulcer can be fully sutured for an hemostatic treatment. When the suturing operation is brought to an end, the suturing apparatus is taken out of the body cavity together with an endoscope.

Figure 9:
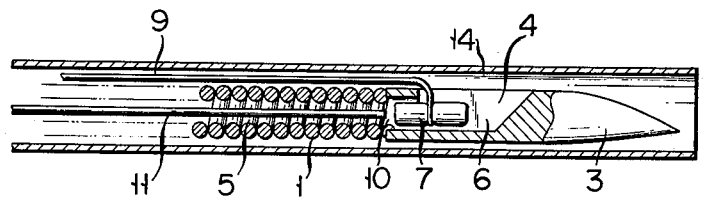

A suturing apparatus according to the embodiment of FIG. 9 comprises not only the suturing apparatus itself of FIGS. 1 and 2, but also a flexible outer tube 14 for receiving the suturing apparatus. When inserted into an endoscope channel, the flexible outer tube 14 prevents the inner wall of the endoscope channel from being abraded by the tubular member 1 of the suturing apparatus which is reciprocated through the endoscope channel. When the suturing apparatus of FIG. 9 is inserted into a body cavity, the needle 3 protrudes from the distal end of the flexible outer tube 14.

Figure 10:
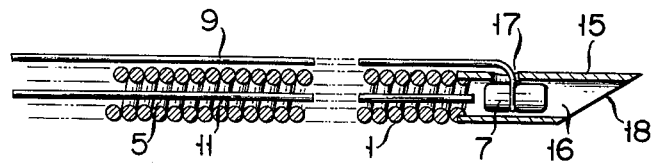

With a suturing apparatus according to the embodiment of FIG. 10, a needle 15 is formed of a hollow cylindrical stainless steel member whose forward end is obliquely out straightway. The suturing thread 9 is extended along the flexible tubular member 1. The leading end of the suturing thread 9 passes through a small hole 17 formed in the lateral wall of the needle 15 to be fastened to a first stop 7. The stop 7 is pushed out of a first-stop receiving chamber 16 formed in the needle 15 and brought ahead of the needle 15 through an opening 18 provided at the forward end of the needle 15.

With the suturing apparatus according to the embodiment of FIG. 11, the needle 15 is not provided with the small hole 17 used in the suturing apparatus according to the embodiment of FIG. 10. Instead, the suturing thread 9 is let to pass through the flexible tubular member 1. This arrangement eliminates the possibility of the suturing thread 9 being caught between the peripharal wall of the tubular member 1 and the inner wall of the endoscope channel.

With the suturing apparatus according to the embodiment of FIG. 12, a flexible pushing tube 19 (it is possible to use a coil tube made of a stainless steel wire) replaces the pushing rod 11 of FIG. 11. The suturing thread 9 is inserted through the pushing tube 19. The arrangement more reliably eliminates the possibility of the suturing thread 9 being caught by any other object.

With the suturing apparatus according to the embodiment of FIG. 13, a flexible outer tube 14 is broadened in diameter. That portion of the suturing thread 9 which is extended out of the first-stop receiving chamber 6 is fitted with a suture-finishing stop 22. A flexible pushing tube 21 such as a coil tube made of a stainless steel wire is inserted into the suturing apparatus from that end of the outer tube 14 which faces the endoscope proximal end. Said end of the outer tube 14 protrudes from the proximal end of the flexible tube 11. The tip of the protruding proximal end of the flexible pushing tube 21 is provided with a knob (not shown). The flexible pushing tube 21 is made to reciprocate by the operation of the knob.

FIG. 14 shows the suture-finishing stop 22 used in the embodiment of FIG. 13. This suture-finishing stop 22 comprises a cylindrical stop housing 24 which is made of rigid plastic material and contains a trancated conical cavity 23 open at the larger diameter end; an end plate 24a which is similarly made of rigid plastic material and fixed to the cylindrical stop housing 24 to close the open larger diameter end of the truncated conical cavity 23; and a truncated conical wedge member 25 which is prepared from an elastic material such as rubber and is tapered in the same manner as the truncated conical cavity 23. That side of the cylindrical stop housing 24 which faces a first stop 7 is provided with a small hole 24b and the end plate 24a is similarly provided with a small hole 24c. The suturing thread 9 passes through these holes 24b, 24c.

When the suture-finishing stop 22 is pushed in the direction of an arrow B shown in FIG. 4, the wedge member 25 leaves the inner wall 26 of the cylinderical stop housing 24 which defines the truncated conical cavity 23. As a result, the suture-finishing stop 22 is moved toward the first stop 7 to decrease a distance therebetween. Conversely, when the suture-finishing stop 22 is pushed in a direction opposite to that of the arrow B, the wedge member 25 is pulled by the suturing thread 9, causing the suturing thread 9 to be clamped between the inner well 26 of the cylindrical stop housing 24 and the peripheral wall of the wedge member 25. A wedge action occurring between both walls prevents the suture-finishing stop 22 from being moved any further in a direction opposite to that of the arrow B.

Figure 16:
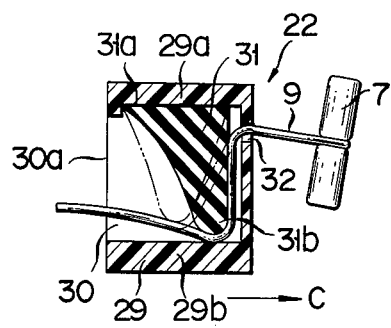
Figure 17:
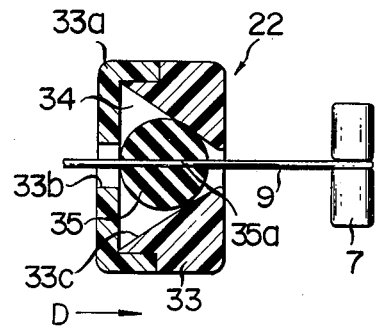

FIGS. 15 to 17 show modifications of the suture-finishing stop 22 of FIG. 14, respectively. The suture-finishing stop 22 of FIG. 15 is formed of a cylindrical member 124 which is prepared from rigid plastic material and contains a conical cavity 28 open at the larger diameter end facing a first stop 7. A conical projection 124a is formed at the center of the opposite side of the cylindrical member 124 to the first stop 7. A small hole 124b formed in the conical projection 124a communicates with the conical cavity 28.

The suturing thread 9 is provided with a plurality of knots 27 which are slightly larger than the aforesaid hole 124b and equidistantly arranged at a space of, for example, 2 millimeters.

When the suture-finishing stop 22 is pushed in the direction of an arrow C indicated in FIG. 15, the knots 27 of the suturing thread 9 are guided by the inner wall of the cylindrical member 124 defining the conical cavity 28 to pass through the small hole 124b, causing the suture-finishing stop 22 to approach the stop 7. Conversely when the suture-finishing stop 22 is moved in a direction opposite to that of the arrow C, a knot 27 lying on the opposite side of the cylindrical member 124 to the first stop 7 is wedged with the inner wall of the conical projection 124a, thereby preventing the cylindrical member 124 from being moved any further in a direction opposite to the arrow C.

The suture-finishing stop 22 of FIG. 16 comprises a hexahedral member 29 which is prepared from rigid plastic material and contains a cavity 30 having a square cross section and open at an opening 30a at one side thereof; and an elastic strip or elastic wedge member 31 which is made of an elastic material such as rubber and received in the cavity 30.

The elastic wedge member 31 is shaped like a tongue. The base end 31a of the wedge member 31 is fixed by means of, for example, adhesive, to the inner surface of one of those side walls 29a of the hexahedral member 29 which are adjacent to an opening 30a of the hexahedral housing 29. The tip 31b of the tongue-shaped wedge member 31 is engaged with the inner surface of the side wall 29b which is placed opposite to that of the aforesaid side walls 29a. The side wall 29c of the hexahedral housing 29 opposite to the opening 30a is provided with a small hole 32 at a point near the side wall 29a. The suturing thread 9 passes through the hole 32.

When the suture-finishing stop 22 is pushed in the direction of an arrow D indicated in FIG. 16, the wedge member 31 is deformed as indicated in a two dots-dash line due to the tensile strength of the suturing thread 9. The tip 31b of the wedge member 31 is separated from the inner surface of the side wall 29b. Accordingly, the suture-finishing stop 22 approaches a first stop 7. Conversely, when the suture-finishing stop 22 is pushed in a direction opposite to that of the arrow D, the suturing thread 9 is clamped between the tip 31b of the wedge member 31 and the inner surface of the side wall 29b, thereby preventing the suture-finishing stop 22 from being moved in a direction opposite to that of the arrow D due to the resulting wedge action.

The suture-finishing stop 22 of FIG. 17 comprises a cylindrical member 33 which is made of rigid plastic material and contains a truncated conical cavity 34 open at both larger and smaller diameter ends; an end plate 33a which is fixed to the cylindrical member 33 to close the larger diameter end of the conical cavity 34 and is provided with a hole 33b at the center; and a spherical member 35 which is made of an elastic material such as rubber and whose peripheral surface abuts against the inner surface 33c of the cylindrical member 33 defining the conical cavity 34. The cylindrical member 33 and the end plate 33a constitute a stop housing. The spherical member 35 is provided with a penetrating passage 35a having a diameter slightly smaller than the thickness of the suturing thread 9 when the spherical member 35 remains in a natural state. The suturing thread 9 is let to pass through the smaller diameter end of the conical cavity 34, the passage 35a penetrating the spherical member 35 and the hole 33b of the end plate 33a.

When the suturing stop 22 is pushed in the direction of an arrow E indicated in FIG. 17, the peripheral surface of the spherical member 35 is removed from the inner surface 33c of the cylindrical member 33, causing the suture-finishing stop 22 to approach a first stop 7. Conversely, when the suture-finishing stop 22 is pushed in a direction opposite to that of the arrow E, the peripheral surface of the spherical member 35 is pressed against the inner surface 33c of the cylindrical member 33, causing the spherical member 35 to shrink. The passage 35a penetrating the spherical member 35 is reduced in diameter and firmly holds the suturing thread 9. Therefore, the suture-finishing stop 22 is prevented from being moved in a direction opposite to that of the arrow E.

Figure 18:
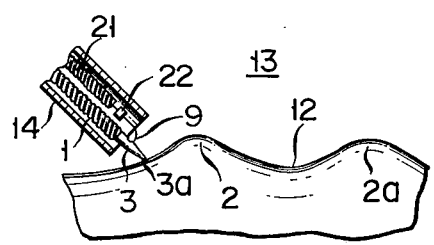
FIGS. 18 to 22 show the sequential steps of progressively suturing tissues around a coeliac bleeding spot by applying the suturing apparatuses of FIGS. 9 to 17.
Figure 19:
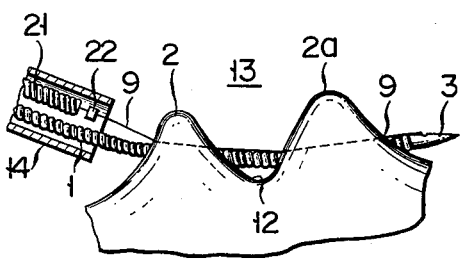
Figure 20:
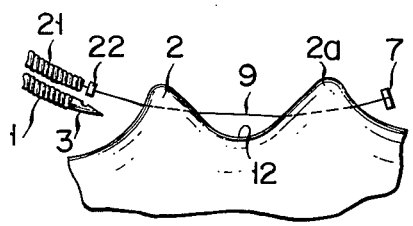

FIGS. 18 to 22 illustrate the manner in which a coeliac bleeding spot is hemostatically treated by the suturing apparatuses according to the embodiments of FIGS. 9 to 17. The suturing steps of FIGS. 18 to 20 are the same as those of FIGS. 3, 4 and 6, description thereof being omitted.

Figure 21:
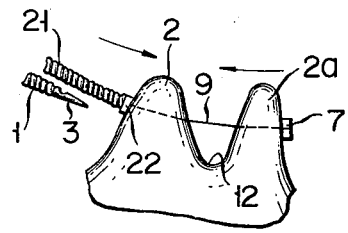
Figure 22:
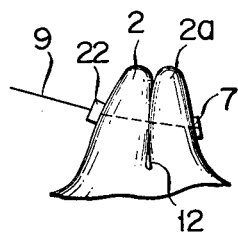

When the suture-finishing stop 22 is pushed by the pushing tube 21 as shown in FIG. 21, after the suturing apparatus is withdrawn from the tissues 2, 2a, the suture-finishing stop 22 approaches the first stop 7 as described with respect to the same unit of FIGS. 14 to 17. As a result, the tissues 2, 2a are respectively drawn nearer to the stop 22, 7, until they are tightly attached to each other, thereby carrying out the hemostatic treatment of the coeliac bleeding spot 12. Thereafter, the suturing thread 9 is cut by the already deseribed process at a point near the suture-finishing stop 22. Since, at this time, the suture-finishing stop 22 is prevented from being moved backward, the suture of the coeliac bleeding spot 12 is reliably sustained.

Figure 23:
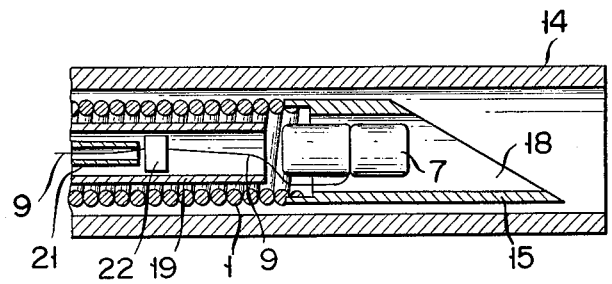
FIG. 23 is a longitudinal sectional view of the distal end portion of a coeliac tissue-suturing apparatus according to another embodiment of the invention.

The coeliac tissue-sutureing apparatus of FIG. 23 in the type in which the suturing apparatus of FIG. 12 is inserted into an outer tube 14, and the suture-finishing stop 22 according to any of the embodiments of FIGS. 13 to 17 is set in front of a separate pushing tube 21 received in the larger pushing tube 19. The outer tube 14 saves an endoscope channel from a damage which might be produced during the reciprocation of the tubular member 1, were it not for the outer tube 14.

Figure 24:
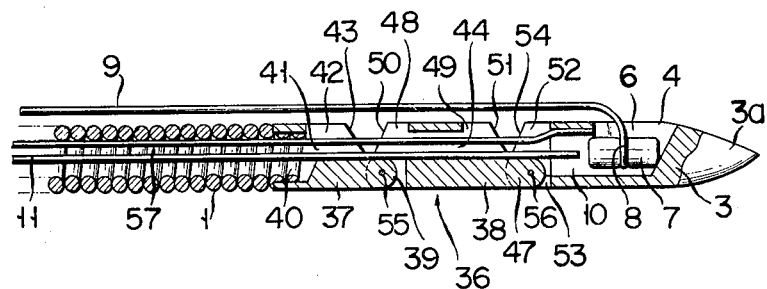
FIG. 24 is a longitudinal sectional view of the main section of a coeliac tissue-suturing apparatus according to a still another embodiment of the invention, which contains a bendable joint.
Figure 25:
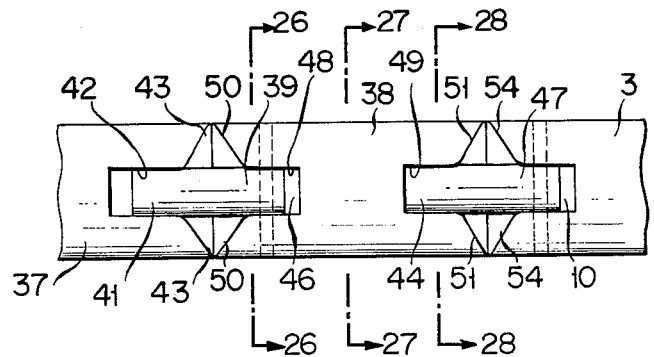
FIG. 25 is a plan view of the bendable joint of FIG. 24.

With the suturing apparatus of FIG. 24, a bendable joint 36 is provided between a needle 3 and a tubular member 1. The bendable joint 36 is formed of two stainless steel cylindrical links 37, 38 (FIGS. 24, 25). The cylindrical link 37 comprises an engagement member 39 which has a substantially square cross section and protrudes from the forward end of the cylindrical link 37 at a point slightly displaced from the axis thereof (FIG. 24). A cylindrical recess 40 is formed at the rear end of the cylindrical link 37 to securely receive the distal end portion of the tubular member 1. A passage 41 having a circular cross section is provided a little above that section of the center line of the suturing apparatus which is defined between the forward end of the cylindrical link 37 and the recess 40. The thin-walled portion of the suturing apparatus along which the passage 41 is extended is provided with a notch 42. The forward end of the notch 42 at which the passage 41 is opened constitutes an inclined plane 43.

Figure 26:
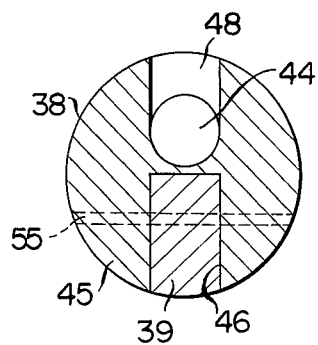
FIG. 26 is a cross sectional view on line 26—26 of FIG. 25.
Figure 27:
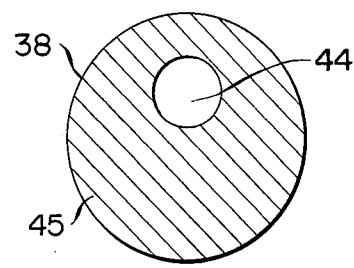
FIG. 27 is a cross sectional view on line 27—27 of FIG. 25.
Figure 28:
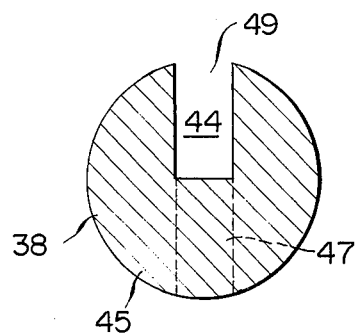
FIG. 28 is a cross sectional view on line 28—28 of FIG. 25.

The cylindrical link 38 is penetrated by a passage 44 having a circular cross section as indicated in FIGS. 26, 27 and 28. A groove 46 is formed at the rear end of the thick-walled portion of the cylindrical link 38 to receive the engagement member 39 of the first mentioned cylindrical link 37. An engagement member 47 having the same shape as the engagement member 39 of the cylindrical link 37 protrudes from the forward end of the thick-walled portion 45 of the cylindrical link 38. Notches 48, 49 are respectively formed in the forward and rear parts of that lateral wall of the cylindrical link 38 which lies opposite to the thickwalled section 45 thereof. Both open end portions of the passage 44 respectively constitute inclined planes 50, 51. Grooves 52, 53 are formed in the mutually facing walls of the rear end portion of the needle 3. The groove 53 is used to receive the engagement member 47 of the cylindrical link 38. That side of the rear end portion of the needle 3 which faces the groove 52 is made into an inclined plane 54.

The cylindrical links 37, 38 and needle 3 are connected together by pins 55, 56 in the order mentioned. The forward end of a flexible pulling rod or bendable control rod 57 made of, for example, a stainless steel coiled wire is fixed to the inner surface of the rear part of the lateral wall of the needle 3. This pulling rod 57 is extended out of the handle 100 (FIG. 1) and can be pulled outward thereby through the circular passages 44, 41 of the cylindrical links 38, 37 which are aligned with each other.

Figure 29:
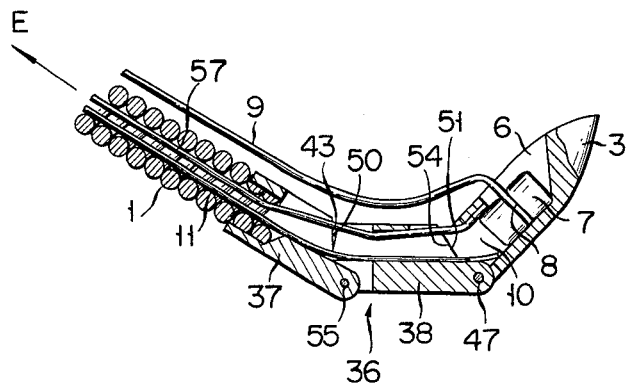
FIG. 29 is a longitudinal sectional view of the joint of FIG. 24 when it is bent.

When the pulling rod 57 is pulled in the direction of an arrow F indicated in FIG. 29, a distance between the inclined plane 43 of the cylindrical link 37 and the inclined plane 50 of the cylindrical link 38, and also a distance between the inclined plane 51 of the cylindrical link 38 and the inclined plane 54 of the needle 3 are shortened, causing the bandable joint 36 to be bent in one direction as illustrated in FIG. 29. Said bending is chosen to be carried until the above-mentioned mutually facing inclined planes abut against each other.

The sutering apparatus according to the embodiment of FIG. 24 is adapted for the suture of relatively flat tissues around a coeliac bleeding spot.

Figure 30:
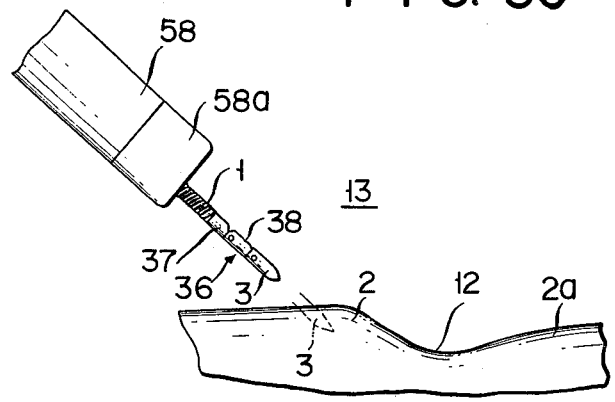
FIGS. 30 to 34 illustrate the sequential steps of suturing tissues around a coeliac bleeding spot by applying the suturing apparatus of FIG. 24.
Figure 31:
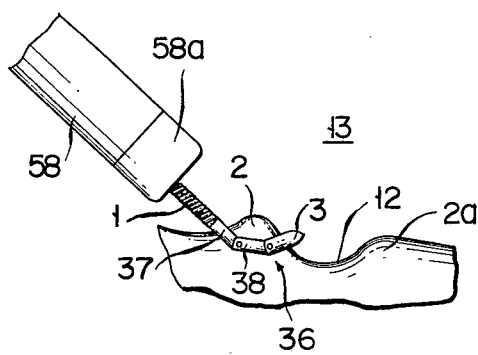
Figure 32:
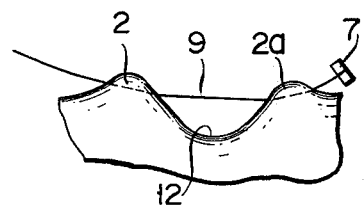
Figure 33:
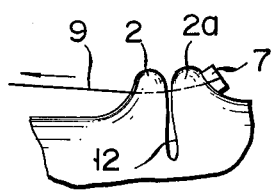
Figure 34:
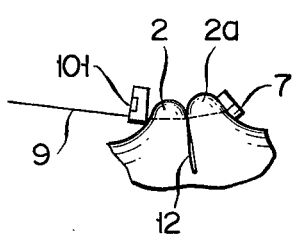

There will now be described by reference to FIGS. 30 to 34 the operation of the embodiment of FIG. 24. A distal end portion of the suturing apparatus is protruded from a distal end 58a of an endoscope 58 with the notches 42, 48, 49 formed on the opposite side of the suturing apparatus to the wall of an body cavity 13. As shown in FIG. 30, the needle 3 is inserted, as indicated in a dot-dash line, into those portions of tissues 2 around a caeliac bleeding spot which lie close to the endoscope 58. When the pulling rod 57 is pulled and the tissues 2 are raised, the suturing apparatus is pushed out of the distal end 58a of the endoscope 58. Then, the tissues 2 are pierced by the distal end portion of the suturing apparatus in a state raised as illustrated in FIG. 31. Thereafter, the suturing apparatus is pushed forward with the bendable joint 36 bent to a smaller extent. The needle 3 is inserted into the tissues 2a lying beyond the coeliac bleeding spot 12. The tissues 2a are raised by the same process as applied to the tissues 2 and pierced by the distal end portion of the suturing apparatus. Thereafter, the pushing rod 11 is pushed to force the first stop 7 out of the needle 3. When the suturing apparatus is pulled out of the tissues 2, 2a, the suturing thread 9 indicates a state piecing these tissues 2, 2a. The operation of suturing the coeliac bleeding spot 12 proceeds, as illustrated in FIGS. 33 and 34, in the same manner as in the case of FIGS. 7 and 8, description thereof being omitted.

Figure 35:
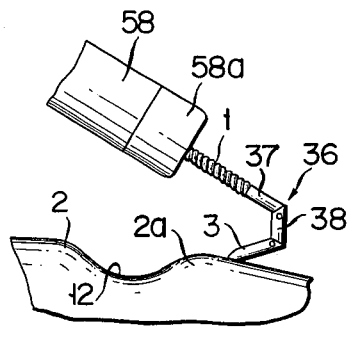
FIGS. 35 to 38 indicate the sequential steps of suturing tissues around a coeliac bleeding spot by a different procese of applying the suturing apparatus of FIG. 24.
Figure 36:
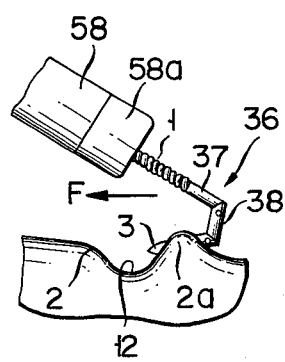
Figure 37:
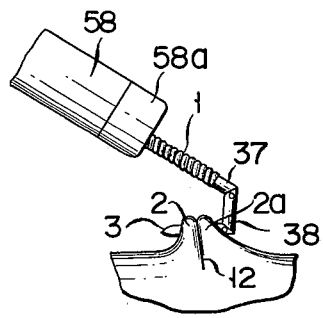
Figure 38:
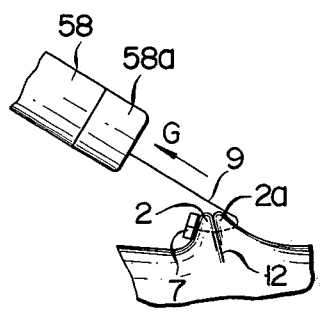

FIGS. 35 to 38 indicate a different manner in which the suturing apparatus of FIG. 24 is applied. The distal end of the suturing apparatus is protruded from the distal end 58a of the endoscope 58 with the notches 42, 48, 49 made to face the wall of a body cavity. The pulling rod 57 is pulled to bend the bendable joint 36 as illustrated in FIG. 35. At this time, the needle 3 is set on tissues 2a. When the suturing apparatus is pulled in the direction of an arrow G indicated in FIG. 36, the tissues 2a are pierced by the needle 3. When the suturing apparatus is further moved in the direction of the arrow G, the needle 3 approaches the tissues 2a while raising them. The needle 3 further pierces the tissues 2 with the tissues around the bleeding spot 12 folded as shown in FIG. 37. Thereafter, while the first stop 7 is pushed out of the needle 3, the suturing apparatus is thrusted out of the distal end 58a of the endoscope 58 and the needle 3 is pulled out of the tissues 2, 2a. The suturing thread 9 is drawn in the direction of an arrow H indicated in FIG. 38 to close the bleeding spot 12. In a similar manner as shown in FIGS. 8 and 31, the clip 101 clamps that portion of the suturing thread 9 which lies adjacent to the surface of the opposite side of the tissues 2a to the bleeding spot 12, thereby completing the suturing operation.

Figure 39:
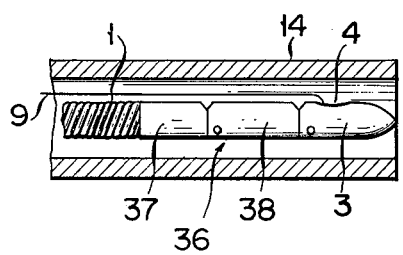
FIGS. 39 to 41 are, respectively, the longitudinal sectional views of the main sections of coeliac tissue-suturing apparatuses according to further embodiments of the invention.

FIG. 39 shows the suturing apparatus of FIG. 24 inserted into an outer tube 14 similar to that of FIG. 9. The outer tube 14 is provided for the same reason as given with respect to the embodiment of FIG. 9, description thereof being omitted.

Figure 40:
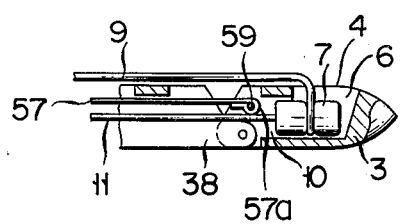

A suturing apparatus according to the embodiment of FIG. 40 is the type in which the forward end of the pulling rod 57 is provided with a loop 57a, which is hung, where required, on a pin 59 fixed to the inner wall of the rear end portion of the needle 3.

Figure 41:
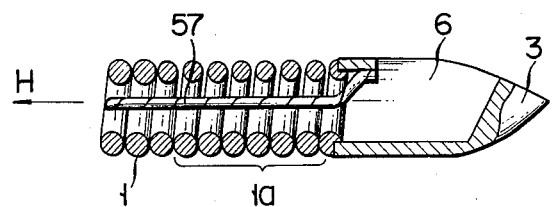
Figure 42:
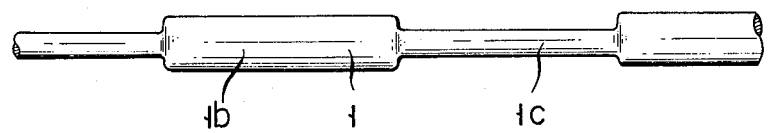
FIG. 42 is an expansion plan of a wire constituting the tubular member of the embodiment of FIG. 41.

A suturing apparatus according to the embodiment of FIG. 41 is the type in which the distal end portion 1a of the tubular member 1 is constructed by first chemically etching the peripheral surface of a wire coiled to form the tubular member 1 such that the etched peripheral surface has an axial section defined by a series of thicker sections and thinner sections, and then winding the surface-etched wire into the coil form in such a manner that the central pait of the thicker sections 1b of the respective turns of the coil are arranged adjacent to each other on one lateral side of the coil, and central part of the thinner sections 1c thereof are set adjacent to each other on the opposite lateral side of the coil. When a pulling rod 57 whose distal end portion 1a is fixed to the needle 3 is pulled in the direction of an arrow K indicated in FIG. 41, the distal end portion 1a is bent only toward that side of the coil on which the thinner sections 1c are set. In other words, the distal end portion 1a of the pulling rod 57 constitutes a bendable portion.

Figure 43:
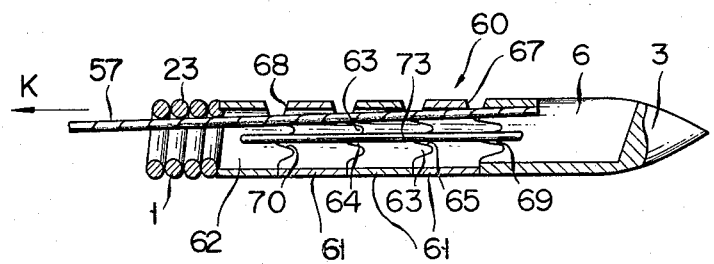
FIG. 43 is a longitudinal sectional view of a coeliac tissue-suturing apparatus according to a further embodiment of the invention.
Figure 44:
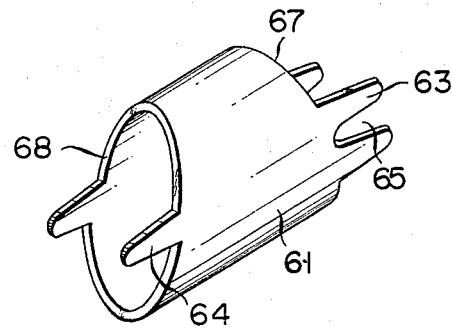
FIG. 44 is an oblique view of an element of the bendable joint of FIG. 43.

With a suturing apparatus according to the embodiment of FIG. 43, a bendable joint 60 comprises a plurality of ring elements 61 and a single ring element 62. One end plane of each ring element 61 is provided with two pair of substantially U or V-shaped engagement projections 63 and a pair of substantially U or V-shaped engagement groove 65 formed therebetween. The opposite end plane of each ring element 61 is provided with a pair of substantially U or V-shaped engagement projections 64 having a smaller apex angle than the angle defined by the adjacent edges of the engaging projections 63. Both end planes of the vertical upper half of the ring element 61 are obliquely cut away as viewed length wise of the ring element 61 to form inclined planes 67, 68. In this case, the mutually facing oblique lines are spaced from each other progressively more widely toward that side of the ring element 61 in which the aforesaid projections 63, 64 and engagement grooves 65, 66 are formed. The rear end plane of the needle 3 and the forward end plane of the last single ring element 62 are respectively provided with a pair of engagement projections 69 having a pair of similar configuration of the projections 64 and a pair of engagement grooves 70 having a similar configuration of the grooves 65.

As shown in FIG. 43, the engagement projections of the needle 3, the ring elements 61 and the last single ring element 62 interlock the corresponding grooves. A pair of flexible, little breakable connecting wires 73 such as stainless steel wires are inserted through the needle 3 and ring elements 61, 62. The corresponding ends of the paired connecting wires 73 are respectively fastened to the inner surface of the rear end of the needle 3 and the inner surface of the last ring element 62 such that the needles 3 and ring members 61, 62 are prevented from being removed from one another.

When the pulling rod 57 whose distal end is fixed to the rear end of the needle 3 is pulled in the direction of an arrow L indicated in FIG. 43, the bendable joint 60 is bent toward that side of the respective ring members on which the inclined planes 67, 68 are formed.

Figure 45:
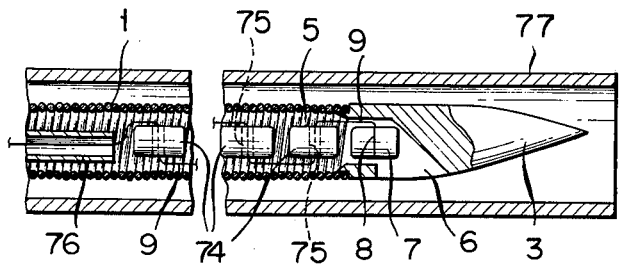
FIG. 45 is a longitudinal sectional view of the main section of a coeliac tissue-suturing apparatus according to a further embodiment of the invention.

Coeliac tissue-suturing apparatuses according the embodiments of FIG. 45 and following drawings illustrate a continuous multistitch suturing operation.

FIG. 45 shows the construction of one of these embodiments. The needle 3 and adjacent tubular member 1 have a construction similar to those of the suturing apparatus of FIG. 1. The difference is that the passage 5 of the tubular member 1 receives solid cylindrical intermediate stops 74 each having a cross bore 75 formed in the middle portion thereof; and the suturing thread 9 whose distal end is fastened to a first stop 7 is extended through the bores 75 of the intermediate stops 74 and then runs through a flexible stop pushing tube 76 inserted into the tubular member 1 and finally out of the proximal end of an endoscope. The stop pushing rod 76 protrudes from the proximal end of the endoscope channel and can be made to reciprocate by an operator's hand as in the preceding embodiments. While being made flexible in conformity to the bend of the endoscope channel, the stop pushing rod 76 has sufficient rigidity to push the stop 7, 74 when inserted into the endoscope channel.

An assembly of the needle 3 and cylindrical member 1 is inserted into an outer tube 77. This outer tube 77 is inserted into the endoscope channel at its proximal end. The rear end of the outer tube 77 protrudes from the proximal end of the endoscope channel, thereby enabling the outer tube 77 to be reciprocated by an operator's hand. The distal end of the outer tube 77 can be moved into or out of the distal end of the endoscope. The outer tube 77 made of coiled stainless steel is rendered flexible in conformity to the bend of the endoscope channel, but has such rigidity that the outer tube 77 is not easily bent when its distal end pushes tissues around a coeliac bleeding spot 12.

Figure 46:
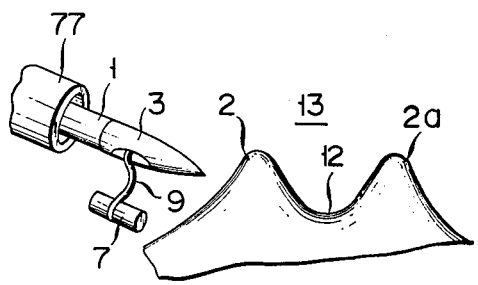
FIGS. 46 to 50 indicate the initial stitch process of suturing tissues around a coeliac bleeding spot by the suturing apparatus of FIG. 45.
Figure 47:
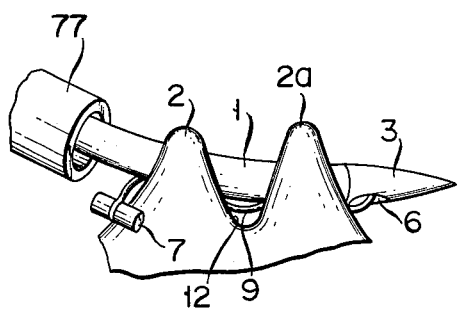
Figure 48:
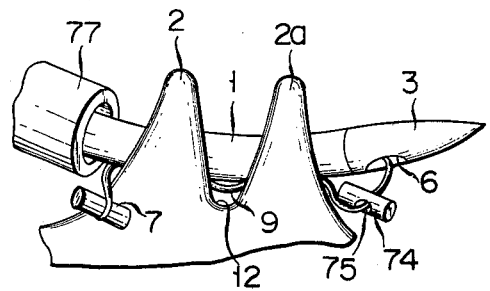
Figure 49:
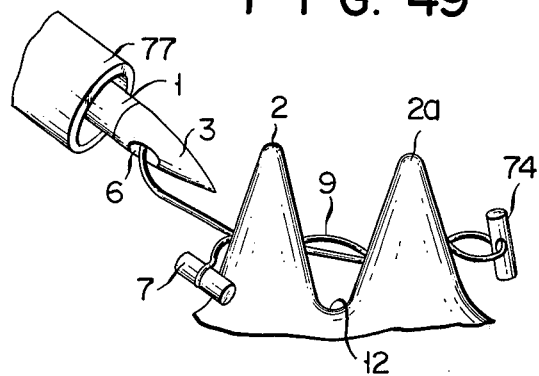
Figure 50:
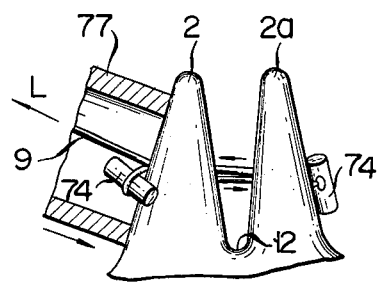
Figure 51:
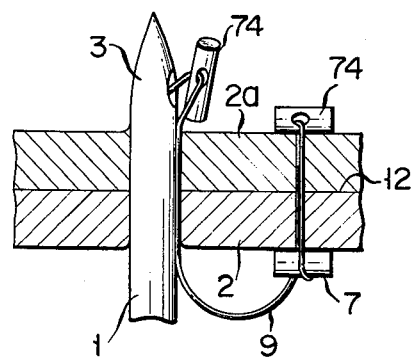
FIG. 51 shows the second stitch process of suturing the tissues.
Figure 52:
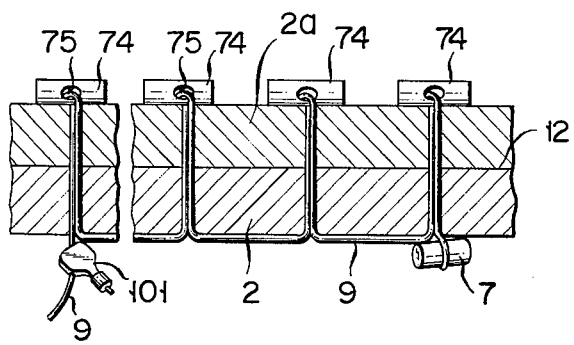
FIG. 52 illustrates the condition in which tissues around a coeliac bleeding spot have been fully sewn up by the suturing apparatus of FIG. 45.

There will now be described the operation of a coeliac tissue-suturing apparatus according to the embodiment of FIG. 45. First, the needle 3 is pushed out of the distal end of an endoscope (FIG. 46) and set near those tissues 2 around the coeliac bleeding spot 12 which lie close to the distal end of the endoscope. The stop pushing tube 76 is driven to force only the first stop 7 out of the nedle 3. Thereafter, the assembly of the needle 3 and tubular member 1 is let to pierce the tissues 2, 2a (FIG. 47). The stop pushing tube 76 is further moved forward (FIG. 48) to force only one intermediate stop 74 out of the needle 3. The assembly of the needle 3 and tubular member 1 is with drawn from the tissues 2, 2a (FIG. 49). At this time the stops 7, 74 are respectively left on the opposite sides of the tissues 2, 2a to the coeliac bleeding spot 12. When the suturing thread 9 is pulled in the direction of an arrow M indicated in FIG. 50 after the outer tube 77 is pushed out of the distal end of the endoscope to be pressed against the tissues 2, the tissues 2, 2a are drawn to each other, and finally abut against each other. FIG. 51 shows the condition in which the needle 3 makes a second stitch. When the needle 3 pierces the tissues 2, 2a, only one of the intermediate stops 74 is forced out of the needle by the stop pushing tube 76. The assembly of the needle 3 and tubular member 1 is withdrawn. The tissues 2, 2a are pressed against each other by the same process as applied in FIG. 50. Thereafter, the same operation as described above is repeated to suture tissues all around the coeliac bleeding spot 12. Finally, the suturing thread is clamped by a clip 101 by the previously mentioned process (FIG. 52) and is cut at a required spot. The above-mentioned procedure enables a broad coeliac bleeding spot 12 to be easily sutured.

Figure 53:
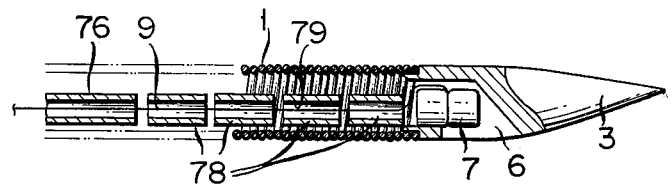
FIG. 53 is a longitudinal sectional view of the main section of a coeliac tissue-suturing apparatus according to a still further embodiment of the invention.
Figure 54:
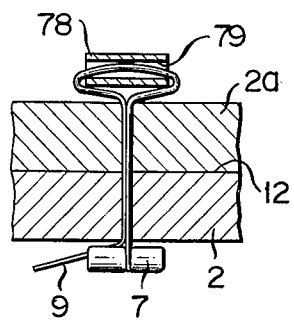
FIG. 54 shows the condition in which tissues around a coeliac bleeding spot have been sewn up by the suturing device of FIG. 53.

With a coeliac tissue-suturing apparatus according to the embodiment of FIG. 53, the intermediate stops 78 are hollow cylindrical members. The suturing thread 9 runs through the lengthwise passages 79 of the cylindrical stops 78. FIG. 54 shows the condition in which the first stitch is made according to the embodiment of FIG. 53. Application of the intermediate stops allows the suturing thread 9 to be extended straight through the tubular member 1 instead of being bent as shown in FIG. 45. When, therefore, any of the intermediate stops 78 is pushed by the stop pushing tube 76, the advantage is that the suturing thread 9 little tends to be caught by any of the intermediate stops 78.

Figure 55:
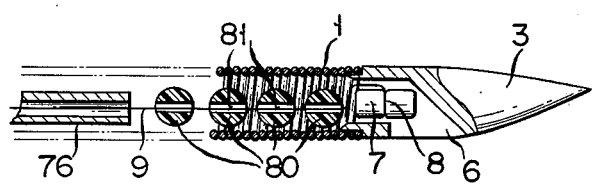
FIG. 55 is a longitudinal sectional view of the main section of a coeliac tissue-suturing apparatus according to a still further embodiment of the invention.
Figure 56:
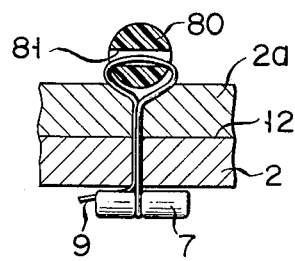
FIG. 56 shows the condition in which tissues around a coeliac bleeding spot have been sewn up by the suturing apparatus of FIG. 55.

With a coeliac tissue-suturing apparatus according to the embodiment of FIG. 55, intermediate stops 80 are solid spheres. A passage 81 penetrates the center of each spherical stop 80 to allow for the run of a suturing thread 9. FIG. 56 shows the condition in which the needle 3 makes a first stitch. In this suturing operation, part of the surface of the spherical intermediate stop 80 bites into the surface of tissues around a coeliac bleeding spot 12, offering the advantage that the suturing operation is unfailingly carried out.

All the stops should advisably be made of plastic material such as polytetrafluoroethylene or silicone rubber which has high resistance to corrosion and is little breakable. With the embodiments of FIGS. 45, 53, 55, it is possible to use the suture-finishing stop 22 of FIGS. 14 to 17 after the last unit of the intermediate stops 78.

What we claim is:

1. A coeliac tissue-suturing apparatus comprising:
   a flexible tubular member having a passage extending therethrough and inserted into a channel of an endoscope;
   a needle having one end concentrically fixed to that end of the tubular member which is inserted into the endoscope and having the other end made into a sharp tip, said needle having substantially the same outer diameter as the tubular member and adapted to protrude from a distal end of the endoscope;
   a first-stop receiving chamber communicating with the atmosphere and the passage of the tubular member;
   a first stop for setting suturing thread on tissues around a coeliac bleeding spot at the commencement of a suturing operation, said first stop being adapted to fix one end of the suturing thread extended along the tubular member, and normally received in the first stop receiving chamber; and
   a pushing member inserted into the tubular member for pushing the first stop out of the first-stop receiving chamber.

2. The coeliac tissue-suturing apparatus according to claim 1, wherein the opposite side of the needle to the tip thereof is provided with a passage which communicates with the first-stop receiving chamber and the passage of the tubular member and receives one end of the first stop, the needle is provided in a lateral side thereof with an opening which communicates with the first-stop receiving chamber and is made large enough to allow for moving the first stop out of and into the first stop-receiving chamber, and an end wall of the first stop-receiving chamber which faces the tip of the needle is formed into an inclined wall which progressively approaches the tip of the needle as the inclined wall is drawn nearer to the opening on the lateral side of the needle.

3. The coeliac tissue-suturing apparatus according to claim 2, wherein the needle and tubular member are received in a flexible outer tube which is conducted through the channel of the endoscope.

4. The coeliac tissue-suturing apparatus according to claim 1, wherein the needle is a hollow cylindrical needle member with a distal end thereof obliquely cut away, and the first-stop receiving chamber is defined by an inner wall of the hollow cylindrical needle member.

5. The coeliac tissue-suturing apparatus according to claim 4, wherein a lateral wall of the needle is provided with a hole through which the suturing thread is guided out of the needle.

6. The coeliac tissue-suturing apparatus according to claim 5, wherein the needle and tubular member are received in a flexible outer tube which is inserted into the channel of the endoscope.

7. The coeliac tissue-suturing apparatus according to claim 4, wherein the suturing thread is extended through the tubular member.

8. The coeliac tissue-suturing apparatus according to claim 7, wherein the pushing member is a tubular member through which the suturing thread passes.

9. The coeliac tissue-suturing apparatus according to claim 1, wherein there is provided between the needle and tubular member a substantially tubular bendable joint which has substantially the same outer diameter as the needle and tubular member, and there is provided a pulling rod which penetrates the bendable joint and tubular member, one end of which is connected to an end of the needle remoter from the tip of the needle and the other end of which is pulled to flex the bendable joint.

10. The coeliac tissue-suturing apparatus according to claim 9, wherein the bendable joint includes a link assembly comprising a plurality of cylindrical links whose adjacent ends are so connected as to allow the benable joint to bend at said ends.

11. The coeliac tissue-suturing apparatus according to claim 10, wherein the link assembly comprises a first cylindrical link, one end of which is fixed to an end of the tubular member disposed adjacent to the needle, and the other end of which is provided with a protruding engagement member, and which comprises an outward inclined end plane formed at a different part of said other end from that at which the protruding engagement member is provided; and a second cylindrical link, one end of which is provided with an engagement groove pivotally engaging the protruding engagement member of the first cylindrical link and is formed with an outward inclined end plane at a different part of said one end from that at which the engagement groove is formed, and the other end of which is provided with a protruding engagement member aligned with the engagement groove and is formed with an outward inclined end plane formed at a different part of said other end from that at which the protruding engagement member is provided; and also wherein a remoter end of the needle than the tip thereof is provided with an engagement groove pivotally engageable with the protruding engagement member of the second cylindrical link.

12. The coeliac tissue-suturing apparatus according to claim 11, wherein the needle, bendable joint and tubular member are received in a flexible outer tube inserted into the channel of the endoscope.

13. The coeliac tissue-suturing apparatus according to claim 10, wherein each of the other cylindrical links than the cylindrical link disposed adjacent to the tubular member is provided on one end thereof with two pairs of first substantially U-shaped engagement projections each pair of which define a substantially U-shaped engagement groove and is also provided on the other end thereof with a pair of substantially U-shaped engagement projections, the cylindrical link disposed adjacent to the tubular member has one end connected to the tubular member and is provided on the other end thereof with a pair of engagement grooves swingably receiving the second substantially U-shaped engagement projections of the corresponding one of the other cylindrical links, facing ends of the adjacent cylindrical links are formed with inclined planes to define a V-shaped space, and the needle is provided on a remoter end thereof from the tip with a pair of substantially U-shaped engagement projections swingably engaging the engagement grooves of the cylindrical link disposed adjacent to the needle.

14. The coeliac tissue-suturing apparatus according to claim 13, wherein the needle, bendable member and tubular member are received in a flexible outer tube inserted into the channel of the endoscope.

15. The coeliac tissue-suturing apparatus according to claim 13, wherein a pair of wires are extended through the cylindrical link assembly on the protruding engagement members and engagement grooves and ends of the wises are respectively fixed to the needle and the link which is disposed closest to the tubular member.

16. The coeliac tissue-suturing apparatus according to claim 9, wherein the bendable member is a coil tube constructed by winding in a coil form a wire comprising alternatingly arranged thicker sections and thinner sections with central portions of the thicker sections set adjacent to each other on one lateral side of the coil and with the thinner sections set adjacent to each other on the opposite lateral side of the coil.

17. The coeliac tissue-suturing apparatus according to claim 16, wherein the needle, bendable member and tubular member are received in a flexible outer tube inserted into the channel of the endoscope.

18. The coeliac tissue-suturing apparatus according to claim 9, wherein one end of the pulling rod is formed into a loop, which is engaged with a pin fixed on an inner wall of the needle.

19. The coeliac tissue-suturing apparatus according to any one of the claims 7 to 18, wherein the suturing thread passes through at least one intermediate stop.

20. The coeliac tissue-suturing apparatus according to claim 19, wherein the intermediate stop is a solid cylindrical member, in which a passage is formed at right angles to the axis of the cylindrical member to allow the suturing thread to run therethrough.

21. The coeliac tissue-suturing apparatus according to claim 19, wherein the intermediate stop is tubular member allowing the suturing thread to pass therethrough.

22. The coeliac tissue-suturing apparatus according to claim 19, wherein the intermediate stop is a solid spherical body, having a passage extended through a center thereof and allowing the suturing thread to run therethrough.

23. The coeliac tissue-suturing apparatus according to claim 19, which comprises a suture-finishing stop through which the suturing thread runs, after passing through the intermediate stop.

24. The coeliac tissue-suturing apparatus according to claim 23, wherein the suture-finishing stop comprises a truncated conical cavity whose shorter diameter end portion is set to face the first stop; a stop housing, one side of which is provided with an opening smaller than a larger diameter section of the truncated conical cavity and the opposite side of which is provided with an opening smaller than the smaller diameter section of the truncated conical cavity, said both openings ensuring communication between the truncated conical cavity and the atmosphere; and a truncated conical wedge member which is received in the stop housing and whose peripheral surface is adapted to abut against an inner wall of the stop housing defining the truncated conical cavity.

25. The coeliac tissue-suturing apparatus according to any one of the claims 7 to 18, which comprises the suture-finishing stop through which the suturing thread passes.

26. The coeliac tissue-suturing apparatus according to claim 23, wherein the suture-finishing stop includes a stop housing which comprises a conical cavity whose base portion facing the first stop is opened and whose apical portion on the opposite side of the conical cavity to the first stop is provided with a small hole having a diameter larger than the thickness of the suturing thread and smaller than the knot of the suturing thread, and a projection surrounding the small hole of the apical portion of the conical cavity.

27. The coeliac tissue-suturing apparatus according to claim 23, wherein the suture-finishing stop comprises a hexahedral housing whose side opposite to the first stop is opened and whose side facing the first stop is provided with a small hole and a tongue-shaped elastic wedge member whose base end is fixed to an inner wall of that side of the stop housing which is positioned adjacent to the side provided with the small hole, and whose forward end is normally elastically pressed against an inner wall of that side of the stop housing which is disposed opposite to said adjacent side.

28. The coeliac tissue-suturing apparatus according to claim 23, wherein the suture-finishing stop comprises a stop housing whose side facing the first stop is provided with an opening which constitutes the smaller diameter end of a truncated conical cavity formed in said stop housing and whose side opposite to the first stop is also provided with a hole; and a solid elastic spherical member in which a passage allowing the suturing thread to run therethrough is extended through a center of said spherical member, and whose spherical surface abuts against the inner wall of the stop housing which defines the truncated conical cavity.

* * * * *